US012597518B2

(12) United States Patent
Sharma et al.

(10) Patent No.: US 12,597,518 B2
(45) Date of Patent: Apr. 7, 2026

(54) INCORPORATING CLINICAL AND ECONOMIC OBJECTIVES FOR MEDICAL AI DEPLOYMENT IN CLINICAL DECISION MAKING

(71) Applicant: SIEMENS HEALTHINEERS AG, Forchheim (DE)

(72) Inventors: Puneet Sharma, Princeton Junction, NJ (US); Philipp Hoelzer, Tokyo (JP); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 405 days.

(21) Appl. No.: 17/449,229

(22) Filed: Sep. 28, 2021

(65) Prior Publication Data

US 2023/0094690 A1    Mar. 30, 2023

(51) Int. Cl.
| | |
|---|---|
| *G16H 50/20* | (2018.01) |
| *G06N 20/00* | (2019.01) |
| *G06T 7/00* | (2017.01) |
| *G16H 10/60* | (2018.01) |
| *G16H 30/20* | (2018.01) |
| *G16H 30/40* | (2018.01) |
| *G16H 40/20* | (2018.01) |
| *G16H 70/20* | (2018.01) |

(52) U.S. Cl.
CPC ............ *G16H 50/20* (2018.01); *G06N 20/00* (2019.01); *G06T 7/0012* (2013.01); *G16H 10/60* (2018.01); *G16H 30/20* (2018.01);

*G16H 30/40* (2018.01); *G16H 40/20* (2018.01); *G16H 70/20* (2018.01); *G06T 2207/20081* (2013.01)

(58) Field of Classification Search
USPC ........................................................ 705/2–3
See application file for complete search history.

(56) References Cited

U.S. PATENT DOCUMENTS

| | | | | |
|---|---|---|---|---|
| 10,599,984 B1 * | 3/2020 | Wubbels | ................ | G16H 30/40 |
| 11,127,506 B1 * | 9/2021 | Jain | ........................ | H04W 4/021 |
| 2008/0171916 A1 * | 7/2008 | Feder | ..................... | G16H 50/20 |
| | | | | 600/300 |
| 2019/0026608 A1 * | 1/2019 | Hsieh | ...................... | G06N 3/045 |
| 2021/0280298 A1 * | 9/2021 | Samset | .................. | G16H 15/00 |
| 2022/0044328 A1 * | 2/2022 | Ligon | .................... | G16H 10/60 |
| 2023/0360778 A1 * | 11/2023 | Cochran | ............... | G06Q 40/08 |

OTHER PUBLICATIONS

Chen, M. (2021). Improved deep learning approaches for medical image analysis (Order No. 31019219). Available from ProQuest Dissertations and Theses Professional. (2902827658). Retrieved from https://dialog.proquest.com/professional/docview/2902827658?accountid=131444 (Year: 2021).*

* cited by examiner

*Primary Examiner* — Bennett Stephen Erickson

(57) ABSTRACT

An AI algorithm may be used in a clinical setting to perform one or more tasks to assist medical personnel. The results produced by the AI algorithm may affect not only patient care, but also the cost of the care. The AI algorithm may be trained on auxiliary data to incorporate the impacts on patient care and cost.

17 Claims, 6 Drawing Sheets

Multiple 'Receiver Operating Characteristic' curves

INCORPORATING CLINICAL AND ECONOMIC OBJECTIVES FOR MEDICAL AI DEPLOYMENT IN CLINICAL DECISION MAKING

FIELD

The following disclosure relates to artificial intelligence for clinical decision making.

BACKGROUND

Artificial intelligence (AI) models may be applied to clinical data, such as medical images, to assess one or more clinical conditions of a patient. In one example, an AI algorithm may review a magnetic resonance image of a patient to determine whether nodules are present. The AI may be trained so that there is a minimal difference between the output of the AI (e.g. the presence or absence of a nodule) and the conclusion reached by a human reviewer. In some cases, the AI performance must meet regulatory guidelines.

Based on the assessment of the AI, the treatment of the patient may be adapted. In the example of the nodules, additional testing may be ordered to investigate the nodules. In this way, the decision of the AI may impact the cost of treatment for the patient.

SUMMARY

By way of introduction, the preferred embodiments described below include methods, systems, instructions, and computer readable media for assessing medical image data using a machine-learned model. A machine-learned classifier, based on auxiliary data, selects a particular machine-learned model or a performance specification of the machine-learned model.

In a first aspect, a method for assessing medical images with a machine-learned model is provided. The method includes receiving, by a processor, first medical image data and first auxiliary patient data, applying, by the processor, the auxiliary patient data to a machine-learned classifier, the machine-learned classifier trained on second auxiliary patient data, selecting, by the processor, the machine-learned model from a plurality of machine-learned models, a performance specification, or the machine-learned model and the performance specification based on applying the first auxiliary patient data to the machine-learned classifier. The machine-learned model operates according to the performance specification, or the machine-learned model is selected based on applying the first auxiliary patient data to the machine-learned classifier. The method includes applying, by the processor, the first medical image data and the first auxiliary patient data to the machine-learned model, generating, by the processor, a medical image result of the medical image based on applying the first medical image to the machine-learned model, and outputting, by the processor, the medical image result.

In one embodiment, the medical image result includes a label, a segmentation, a classification, a registration, a quantification, a fusion image, a simulation, or a combination thereof.

In one embodiment, the machine-learned model is a detection algorithm, a segmentation algorithm, a quantification algorithm, a model, a registration algorithm, a fusion algorithm, a simulation algorithm, or a combination thereof.

In one embodiment, the performance specification includes an operating characteristic curve, an operating point, or a combination thereof.

In one embodiment, the first auxiliary patient data includes patient vital information, patient outcome statistics, available treatment options, medical treatment guidelines, length of stay, treatment cost, reimbursement codes, mistakes made, or a combination thereof.

In one embodiment, the first auxiliary patient data is received from a network interface in communication with a medical data repository.

In one embodiment, the method includes receiving, by the processor, further auxiliary patient data collected based on the medical image result, and updating, by the processor, the machine-learned model based on applying the further auxiliary patient data to the machine-learned classifier.

In one embodiment, the machine-learned classifier and the machine-learning model are integrated into a machine learning network, and the first medical image data and first auxiliary patient data are applied to the machine learning network.

In a second aspect, a medical image assessment system is provided. The system includes an image processor, coupled with a memory containing instructions that, when executed, cause the image processor to: apply first auxiliary patient data to a machine-learned classifier, select a machine-learned model from a plurality of machine-learned models based on output from applying the first auxiliary patient data to the machine-learned classifier, apply the first medical image to the selected machine-learned model, and generate an analysis of the first medical image based on the application of the first medical image to the machine-learned model.

In one embodiment, each machine-learned model of the plurality of machine-learned models is configured with a different operating characteristic curve of a plurality of operating characteristic curves.

In one embodiment, each machine-learned model of the plurality of machine-learned models is configured with a different operating point of a plurality of operating points.

In a third aspect, a method for training a machine-learning model is provided. The method includes receiving, by a processor, auxiliary patient data and a plurality of machine learning specifications associated with the auxiliary patient data, training with machine learning, by the processor, the machine-learning model based on the auxiliary patient data and the machine learning specifications. A result of the training is a machine-learned model, and the machine-learned model is trained to output a machine learning specification. The method includes storing, by the processor, the machine-learned model.

In one embodiment, the plurality of machine learning specifications includes a plurality of operating characteristic curves.

In one embodiment, the plurality of machine learning specifications includes a plurality of operating points.

In one embodiment, the plurality of machine learning specifications includes a plurality of further machine-learned models.

In one embodiment, the method includes applying, by the processor, second auxiliary patient data to the machine-learned model, and generating, by the processor, the output based on the applying. The machine learning specification is based on the second medical image data and the second auxiliary patient data.

In one embodiment, the method includes receiving, by the processor, third auxiliary patient data collected based on the output, and updating, by the processor, the machine-learned classifier based on applying the third auxiliary patient data and the plurality of machine learning specifications to the machine-learned classifier.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
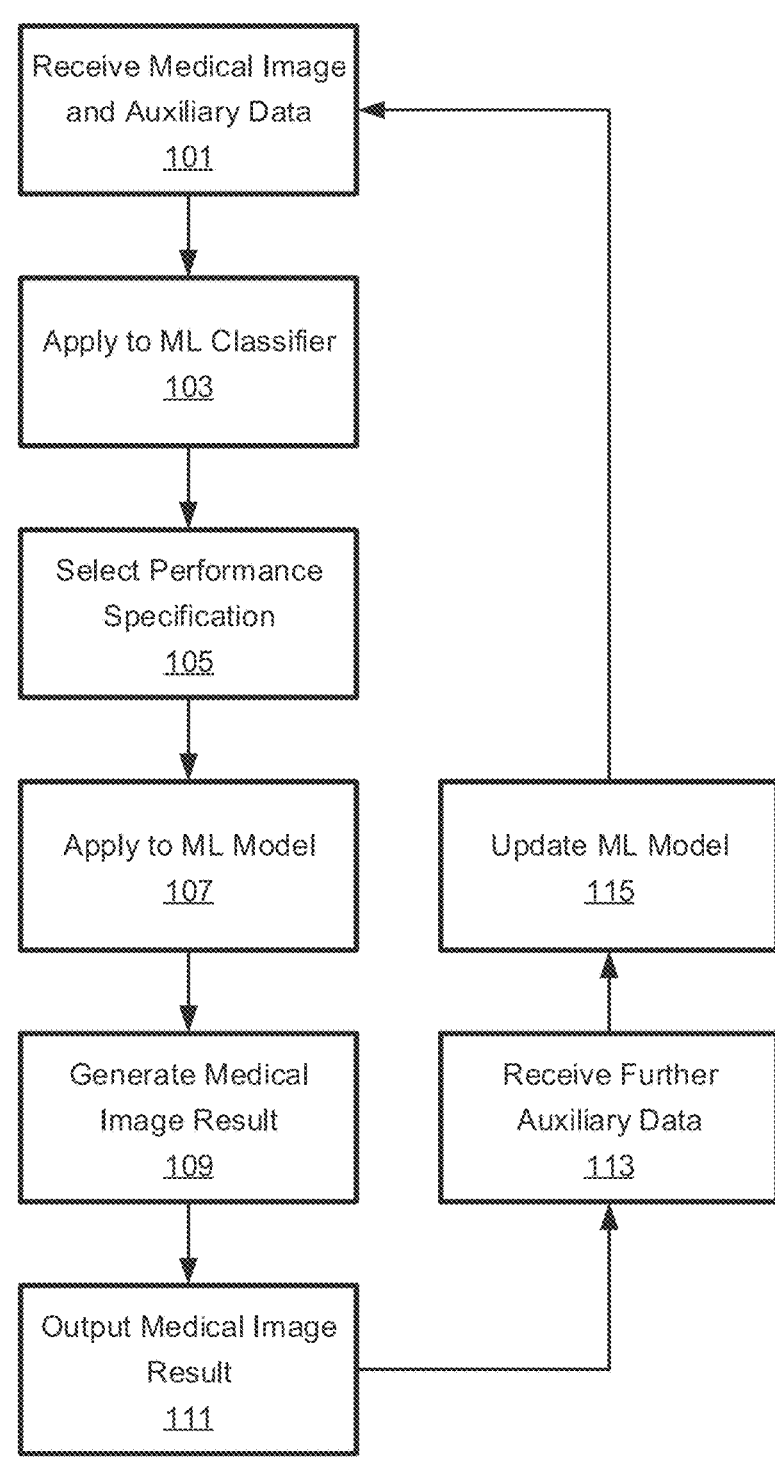
FIG. 1 illustrates an embodiment of a method of assessing medical images.

Artificial intelligence algorithms and machine learning techniques, such as deep learning models, have been developed and trained to assist clinicians by classifying medical images. The AI algorithms may be trained based on a set of images to achieve the classification performance of a human rater reviewing the same images. The goal of training may be to minimize a cost function, such as an amount of disagreement against a human generated ground truth annotation. Additionally or alternatively, the cost may be a sensitivity, a specificity, a diagnostic accuracy, an Area under the "receiver operating characteristic (ROC)" curve (AUC), or another metric.

When deployed in a clinical care pathway, the results produced by the AI algorithm will not only have downstream clinical impact, but also economic impacts. In some cases, AI produced results may trigger additional testing (e.g. more imaging exams), while in some other cases, the AI results may result in a fewer number of diagnostic exams.

The cost of care for a patient may be impacted, positively or negatively, by the decision of the machine-learned model. For example, based on the result provided by the machine-learned model, unnecessary treatment may be ruled out, appropriate treatment may be selected, the patient may be discharged or transferred to a specialized or more general care facility, diseases may be detected early, and an intervention may be performed in a timely manner.

Current medical imaging AI algorithms are developed without consideration of the economic effects of the results generated by the algorithms, either in training or during deployment. In some cases, clinicians review the results provided by the AI algorithm (e.g. to guide treatment based thereon), but not the AI algorithm itself.

AI algorithms in a clinical setting are subject to regulatory approval before use. The approval process verifies that the algorithm provides adequate clinical utility (e.g. sufficient safety and efficacy). However, the regulations do not consider intended or unintended economic consequences of the safe and effective results generated by the AI decision or output.

If the AI decision is linked to a downstream clinical decision to order or not order a diagnostic test, for example, a machine-learning model may be trained using multitask learning with a high diagnostic metric (e.g. sensitivity, specificity, and/or accuracy) in conjunction with optimizing other downstream criteria (e.g. appropriate tests, economic costs).

In some cases, a machine-learned model may include multiple sets of performance or machine learning specifications (such as multiple ROCs or multiple operating points). In some other cases, a communication gateway between the algorithm and medical software may retrieve relevant information such as a patient outcome, treatment guidelines, and reimbursement codes. The medical software may include picture archiving and communications system (PACS), radiology information system (RIS), hospital information system (HIS), electronic hospital record (EHR), electronic medical record (EMR), scheduling software, computerized physician order entry, billing/coding/auditing software, and practice management software. Communication between the machine-learned model and the medical software may be established via HL7, DICOM, the internet, mobile communication, or other means. In still some other cases, a classifier may select one of multiple performance specifications or machine learning specifications based on auxiliary input data, such as patient information, medical records, hospital standard practice, or other information. Additionally or alternatively, changes in the auxiliary input data may be monitored and a closed feedback loop may be used to update the models based on the changes.

The AI algorithm may perform one or more tasks in the clinical environment. For example, the algorithm may detect the presence or absence of a specified feature (e.g. a nodule or cancerous tissue) in a medical image. In another example, the algorithm may perform classification, registration, fusion, simulation, or another task on an input medical image. The structure of the algorithm may be based on deep learning (e.g. a deep belief network, ResNet, DenseNet, Autoencoder, capsule network, generative adversarial network, Siamese network, convolutional neural network, or deep reinforcement learning) or other machine learning techniques (e.g. a support vector machine, Bayesian model, decision tree, or k-means clustering).

Once trained, the AI algorithm (e.g. a machine-learned classifier or machine-learned model) may use an augmented area under the curve (AUC) decision boundary that considers the total cost of development of an algorithm.

In one example, an existing algorithm (e.g. a classifier or other algorithm that has been granted regulatory approval based on performance) is tuned for each hospital according to the individual constraints of the environment. The operating point of the algorithm may be reviewed after tuning to ensure the performance is still within the limits for regulatory approval. The algorithm tuning may be performed at a hospital or at a vendor site. Additional data and further training may be applied to the algorithm during tuning for one hospital, while not for another. For example, fungi that masquerade as pulmonary nodules are often seen in southern states of the United States but are not as common in northern states. Training the algorithm with cases including the fungi may help increase the specificity of the algorithm.

In another example, the algorithm may be adapted to various economic and clinical environments. Reimbursement rates for healthcare and treatment guidelines are economic and clinical environments that differ over time and between different hospitals, so different operating points of the algorithm may be useful for hospitals in different states. Data collected over time (e.g. resources spent, tests ordered, mistakes made) may be used to improve the AI algorithm. A feedback loop may be used so that further data is collected and used to update or improve the algorithm. The auxiliary data may be any indicator of clinical and/or economic impact (e.g. length of hospital stay and cost and/or length of procedure). For example, if the stage distribution of lung cancer is biased towards stage iv, then stricter nodule detection rules may be desired for the algorithm. If stage i lung cancer is dominant, the detection criteria may be relaxed to reduce unnecessary biopsies.

Other conditions in addition to lung cancer may benefit from the adaptation of the AI algorithm. For example, pulmonary nodules may develop into lung cancer and, accordingly, are best detected as early as possible to maximize treatment success. However, most of the nodules found on computed tomography (CT) images are benign, so a well-balanced assessment middle ground between early intervention and overtreatment may be appropriate. In clinical practice, many institutions define different thresholds for the follow up of the incidentally found nodule (e.g. >6 mm according to the Fleischner guidelines) and for the oncology related cases (e.g. post cancer treatment) where the accurate detection of even the smallest nodules is of utmost importance. Similarly, in lung cancer screening exams, follow up is mandated only for larger nodules (>6 mm). If, however, a new nodule of smaller size newly emerges, there is an increase likelihood of malignancy.

Additionally, calcification in the coronary territories is a strong predictor of cardiovascular disease. The relevance of this biomarker is, however, age dependent. An AI algorithm may be able to incorporate age or other patient information to trigger appropriate patient management.

Further, in the case of Alzheimer's, there is growing evidence that hippocampal atrophy is strongly associated with the onset of Alzheimer's disease. While Alzheimer's may be detected early, even incidentally, from MRI images, the lack of appropriate treatment options renders this diagnosis ineffective. Currently, there is one disease modifying treatment pending FDA approval (Aducanumab). An AI algorithm is able to query information sources and, based upon the availability of treatment options, may alert the radiologist to an atrophy in the hippocampus.

From these examples and the disclosure, it may be seen that appropriate patient management is highly contextual. Training AI algorithms on medical data as well as the treatment and economic data may help incorporate the context into an output of the AI algorithm.

FIG. 1 illustrates an embodiment of a method classifying medical images. More, fewer, or different acts may be performed. In some cases, acts 113 and 115 may be omitted. A processor coupled to a memory may be configured to perform one or more of the acts. For example, the processor 603 of FIG. 6 may be configured to perform one or more of the acts of FIG. 1. One or more acts of FIG. 1 may correspond to acts or elements of the method illustrated in FIG. 2.

Figure 2:
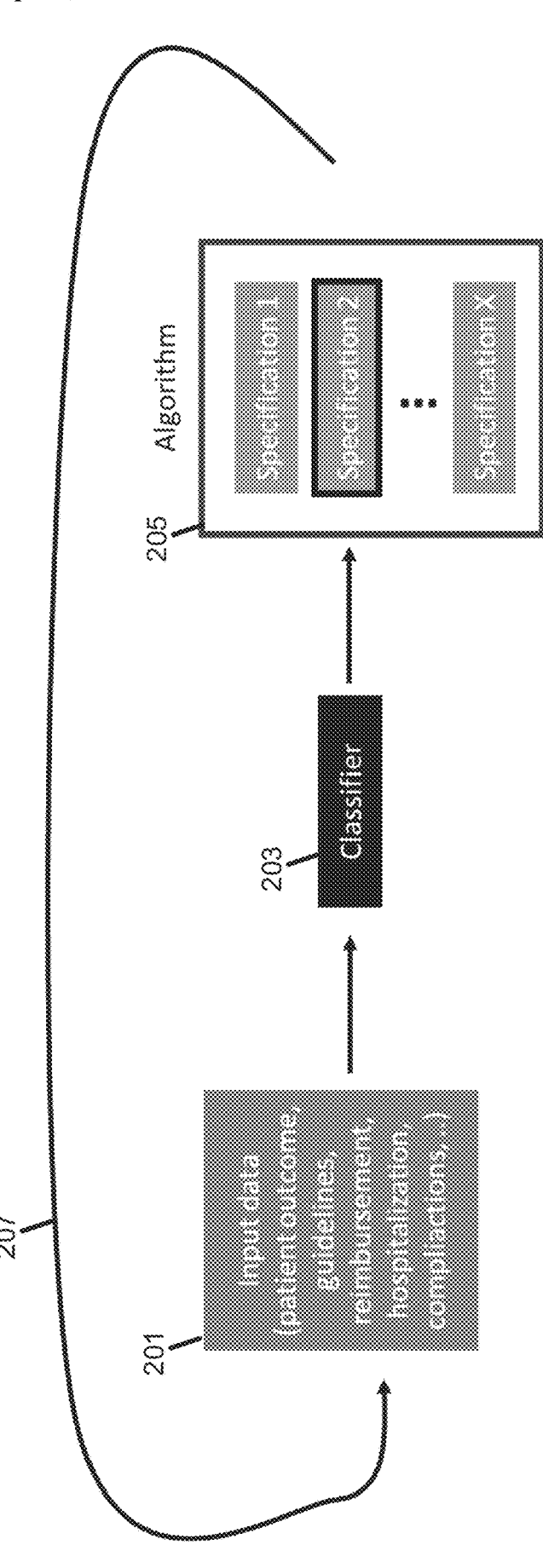
FIG. 2 illustrates another embodiment of a method of assessing medical images.

In act 101, input data is received (e.g. the data 201 of FIG. 2). The input data may include a medical image and/or auxiliary patient data. The medical image may be generated by a medical imager. For example, the medical imaging device 609 of FIG. 6 may generate the medical image. The image may be received directly from the medical imager or through one or more intermediaries. In some cases, the medical image is received from the medical imager or a computer over a network. In some other cases, the medical image is stored and later received. For example, a server may store medical images and send or load the medical images for classifying.

The medical image may be an x-ray image, a computed tomography (CT) image, a magnetic resonance (MR) image, or another image. The medical image may depict anatomy. For example, the medical image may depict a torso, head, or other portion of anatomy. In some cases, the medical image may be part of a training dataset of medical images.

The auxiliary information and/or the medical image data may be received from a medical information repository. A gateway or network adapter, such as the network adapter 607 of FIG. 6, may receive the auxiliary information. The auxiliary information may include patient vital information (e.g. height, weight, age, medical history), patient outcome statistics, available treatment options, medical treatment guidelines, length of stay, treatment cost, reimbursement codes (e.g. resources spent and tests ordered), and/or mistakes made.

In act 103, the auxiliary data is applied or input to a machine-learned classifier (e.g. the classifier 203 of FIG. 2). The machine-learned classifier may be trained on another set of auxiliary patient information, a plurality of performance specifications, and/or an identifier of one or more machine-learning models. The other auxiliary patient information, a plurality of performance specifications, and/or an identifier of one or more machine-learning models may be referred to as a training dataset. The machine-learned classifier is configured to receive as input the auxiliary patient data.

In act 105, a performance specification or machine learning specification is selected based on applying the auxiliary information to the machine-learned classifier. The selection may be made from a plurality of known machine-learning models, ROC curves, and/or operating points, as represented by the set 205 of specifications in FIG. 2. In one case, the performance specification identifies a particular machine-learned network (e.g. from a plurality of machine learned networks available) to which the medical image data may be applied (e.g. in act 107). Additionally or alternatively, the performance specification may comprise a ROC curve and/or and operating point. A machine-learned model (e.g. the machine-learned model of act 107) may be configured to operate according to the ROC curve and/or the operating point.

In act 107, the medical image data is applied to a machine-learned model. The machine-learned model may have been trained on another set of medical image data. The other medical image data may be referred to as a training set of image data. The machine-learned model may be a detection algorithm, a segmentation algorithm, a quantification algorithm, a model, a registration algorithm, a fusion algorithm, a simulation algorithm, or another algorithm configured to process medical image data. In one case, the machine-learned model may be a machine-learned model operating according to the selected ROC curve and/or operating point. Additionally or alternatively, the machine-learned model may be the machine-learned model selected by a machine learning classifier.

Figure 4:
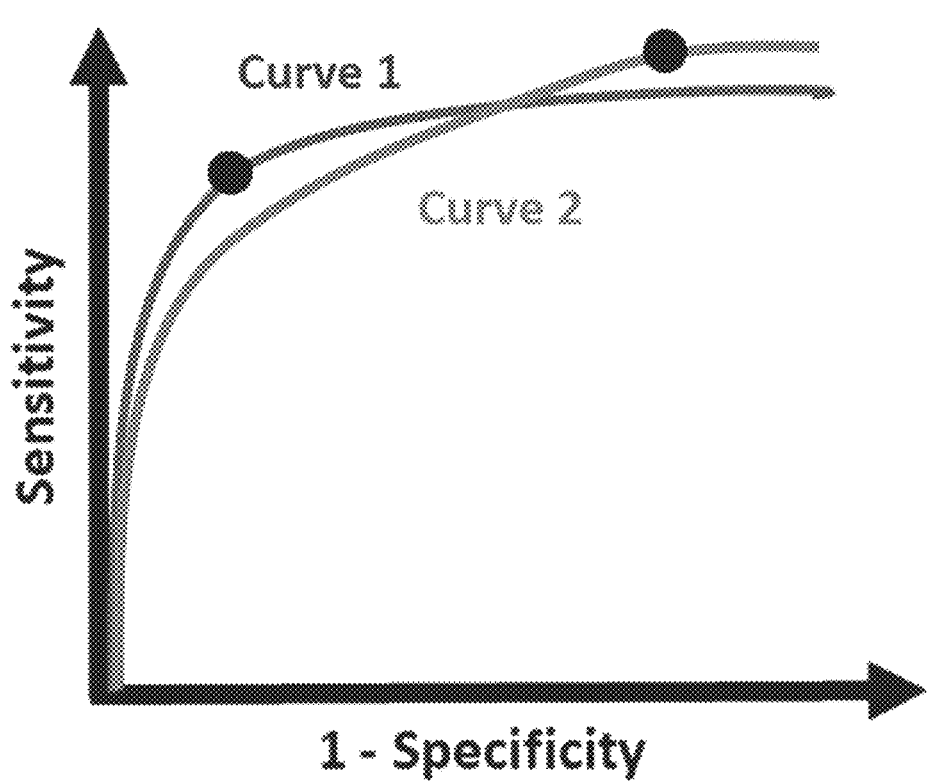
FIG. 4 illustrates multiple example receiver operating characteristic curves.
Figure 5:
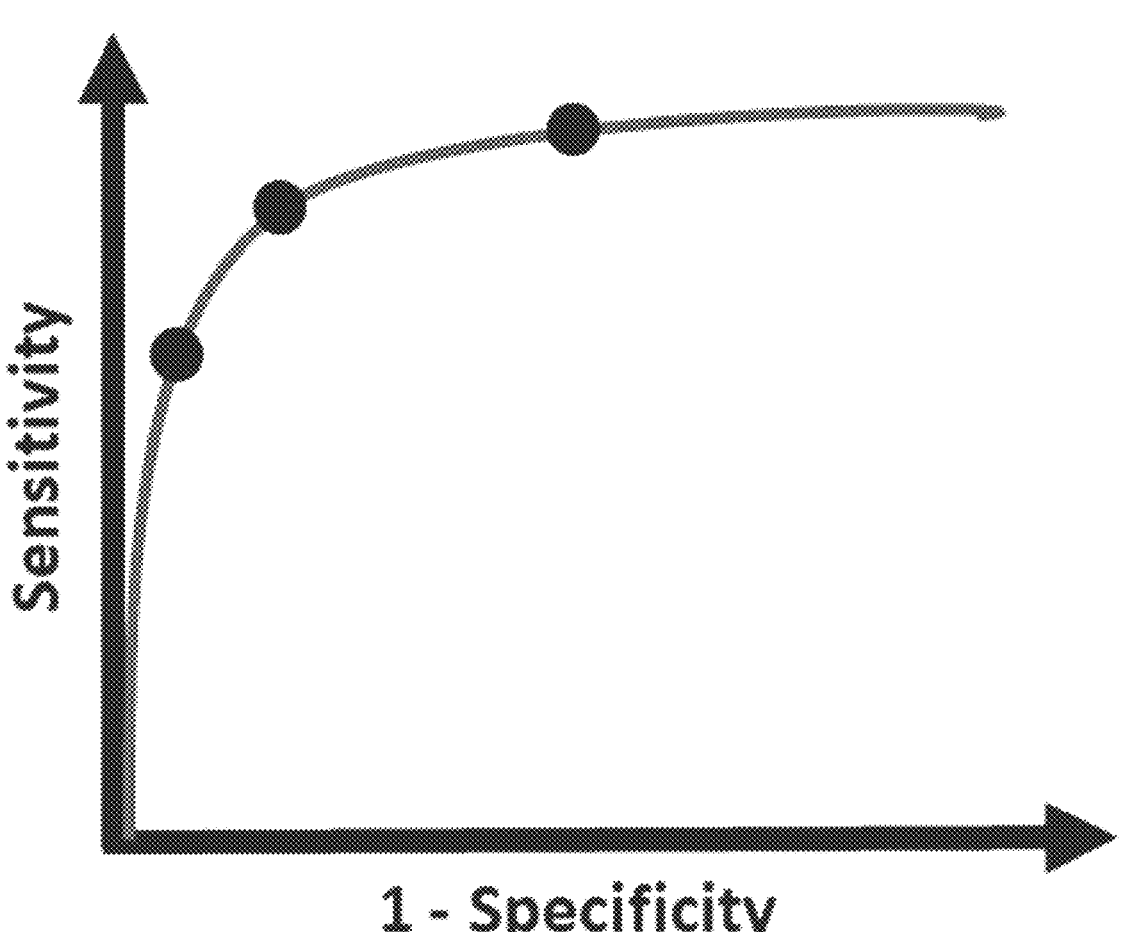
FIG. 5 illustrates multiple example operating points.

The receiver operating characteristic curves and operating points are illustrated in FIG. 4 and FIG. 5, respectively. In FIG. 4, multiple ROC curves are shown. The horizontal axis is 1 minus the specificity of the model, and the vertical axis is the sensitivity of the model. The dots on the curves represent the specificity and sensitivity of the model applied to the input medical image data according to the ROC curve.

Depending on the auxiliary data, the machine-learned classifier may select an appropriate ROC curve. Though there are two ROC curves illustrated, additional ROC curves for the downstream machine-learned models may be specified. In this way, the classifier may output or select a ROC curve from a plurality of ROC curves with different sensitivities. The same medical image data applied to the machine-learned model may output a different result depending on which selected ROC curve the machine-learned model is configured to operate according to. Because the context embodied in the auxiliary data may make different sensitivities appropriate (e.g. for identifying nodules or calcification extent), the operation of a downstream machine-learned model is then tailored to the context (e.g. by selection of a particular model and/or configuration of a model according to the selected performance specification).

In FIG. 5, multiple operating points on the same curve are shown. The machine-learned classifier, based on the auxiliary data, may select one of the operating points for the downstream machine-learned model. The dots on the single curve represent different pairs of specificity and sensitivity applied to input medical image data by the machine-learned model.

For the different ROC curves or operating points on the same curve, the outcome of the machine-learned model may be checked to see that the model continues to comply with regulations in each case. In this way, it may be ensured that the context added to the machine-learned model (e.g. by the classifier selecting the ROC curve or operating point by which the machine-learned model operates) has not resulted in non-compliance. For example, the training dataset (e.g. of medical image data and medical image results) used to train the machine-learning model may be applied to the model operating according to the different ROC curves and operating points to determine whether the model achieves regulations for, in one case, accuracy.

In act 109, a medical image result or analysis of the medical image is generated. The machine-learned model may output the result. The medical image result may be any assessment or analysis task performed on the image. For example, the result may include a label, a segmentation, a classification, a registration, a quantification, a fusion image, and/or a simulation. In this way, the particular machine-learning model or performance specification may be applied to a variety of tasks in a clinical setting.

Because the auxiliary data is applied to the ML classifier (e.g. in act 103) and guides the process by the selection of the performance specification and/or machine-learning model, the image processing task (e.g. the medical image result) is generated considering a context of the medical image data.

In some cases, a machine-learned network may incorporate both the machine-learned classifier and the machine-learned model. The network may be referred to as a "monolithic network." The medical image data and the auxiliary image data may be applied together to the network (e.g. as described with respect to acts 103 and 107). The network may be configured to select a particular performance specification, such as a ROC curve or an operating point, and generate the medical image result (e.g. as described with respect to act 109) according to the performance specification.

In act 111, the medical image result is output. The medical image result may be output with the medical image data, the selected machine-learned model, and/or the selected performance specification. The medical image result, medical image data, the selected machine-learned model, and/or the selected performance specification may be output to a display. For example, the display 611 of FIG. 6 may display the medical image data medical image data, the selected machine-learned model, and/or the selected performance specification.

The machine learning classifier may be updated. The updating may be accomplished by a feedback loop (e.g. the loop 207 of FIG. 2) where the performance of the classifier is used to train the classifier again. New or changing auxiliary data may be reflected by the updated classifier. Additionally or alternatively, the machine learning classifier may be updated or tuned based on auxiliary data for a particular region and/or healthcare facility. As discussed above, the particular prevalence of disease (e.g. fungi, lung cancer stages), reimbursement rates, treatment guidelines, or other auxiliary data may form a basis for the updating. The machine learning classifier may be updated at regular or irregular intervals to ensure the new auxiliary data (e.g. context) is incorporated into the classifier.

In act 113, further auxiliary data is received. The further auxiliary may be collected over time. In some cases, the auxiliary data may be related to or based on the output (e.g. medical image result) of the machine-learned model (e.g. as selected by the classifier or operating according to the ROC curve or operating point selected by the classifier). In this way, the machine-learned classifier may be self-optimized.

In act 115, the machine-learned classifier is updated using machine learning. The updating may be performed by retraining the machine-learned classifier on the new, changed, or further auxiliary data. By training the classifier on auxiliary data that is not part of the training dataset of auxiliary data used to previously train the machine-learned classifier, new or additional context may be incorporated.

Figure 3:
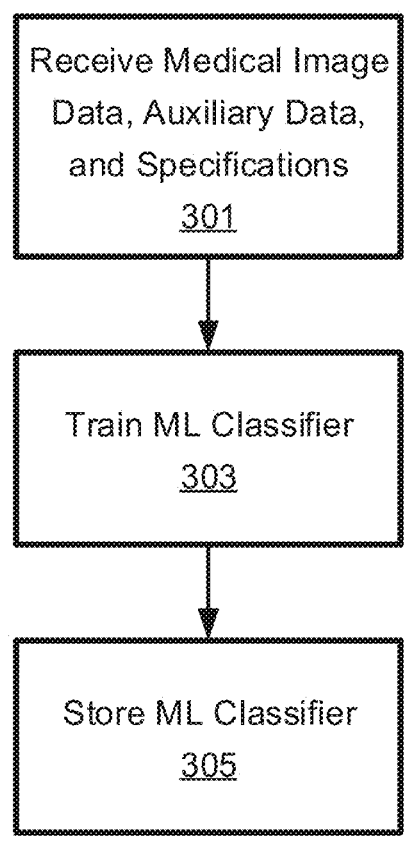
FIG. 3 illustrates an embodiment of a method for training a machine learning network to assess medical images.

FIG. 3 illustrates an embodiment of a method for training a machine learning classifier to select a machine-learned model or performance specification (also known as a machine learning specification). In some cases, other acts may precede or proceed from the acts of FIG. 3. For example, one or more acts of FIG. 1 may proceed from act 305 of FIG. 3 or another act. In another example, acts 301, 303, and 305 may proceed from act 111 of FIG. 1. A processor coupled to a memory may be configured to perform one or more of the acts. For example, the processor 603 of FIG. 6 may be configured to perform one or more of the acts of FIG. 3.

In act 301, auxiliary data, medical image data, and/or machine-learning/performance specifications are received. The auxiliary data may be received from a medical information repository. For example, a gateway or network adapter, such as the network adapter 607 of FIG. 6, may receive the auxiliary information. The auxiliary information may include patient vital information (e.g. height, weight, age, medical history), patient outcome statistics, available treatment options, medical treatment guidelines, length of stay, treatment cost, reimbursement codes (e.g. resources spent, and tests ordered), and/or mistakes made.

In some cases, the auxiliary data may be annotated with a performance specification or an identity of a machine-learning model. The identity may be a reference to an existing machine-learned model to which the medical image data is to be applied. In one case, the identity may be a reference to a particular type or architecture of a machine-learned model. The performance specification may include a ROC curve or operating point associated with the auxiliary data. In this way, the classifier is trained to, based on the input data, select the appropriate machine-learned model, ROC curve, and/or operating point for performing the desired medical task (e.g. generating the desired medical image result) given the context in the auxiliary data.

The auxiliary data used to train the machine learning classifier may be referred to as a training dataset. In one case, when a machine-learned classifier is being trained (e.g. updated), the auxiliary data may be the further auxiliary data received according to act 113 of FIG. 1.

In the case of a "monolithic" machine learning network, the medical data is also received. Through training with machine learning, the machine learning network may learn to map both the input medical imaging data and the auxiliary data to a selection of an appropriate machine-learning model and/or performance specification as well as a medical image result. For the monolithic machine learning network, the received auxiliary data and medical image data may be annotated with a performance specification, an identity of a machine-learning model, and a medical image result.

In act 303, a machine learning classifier may be trained using machine learning. The auxiliary data and associated performance specifications and/or machine-learning model identities may be applied to the machine learning network (or, for the monolithic machine learning network, the auxiliary data and medical image data as well as the associated performance specifications, machine-learning model identities, and/or medical image results). The machine learning network may be a deep learning network, such as a neural network.

A result of the training is a machine-learned classifier. The machine-learned classifier may accept as input a medical image and output a performance specification and/or identity of a machine-learned model to be applied to medical image data.

In act 305, the machine-learned classifier is stored. The machine-learned classifier may be stored for later retrieval for classification of an image of a given patient. The machine-learned classifier may be stored in a memory. For example, the machine-learned classifier may be stored in the memory 605 of FIG. 6.

Once trained, further auxiliary data (e.g. "unseen" auxiliary data not part of the training set) may be applied to the machine-learned classifier. Based on the applying, the machine-learned classifier may output a performance specification and/or a machine-learning model based on the auxiliary data. The further auxiliary data may be classified according to one or more of the acts of FIG. 1. For example, a machine learning classifier trained according to FIG. 3 may be the machine-learned classifier of FIG. 1 (e.g. acts 103, 105, or other acts) and/or FIG. 2 (e.g. element 203).

Figure 6:
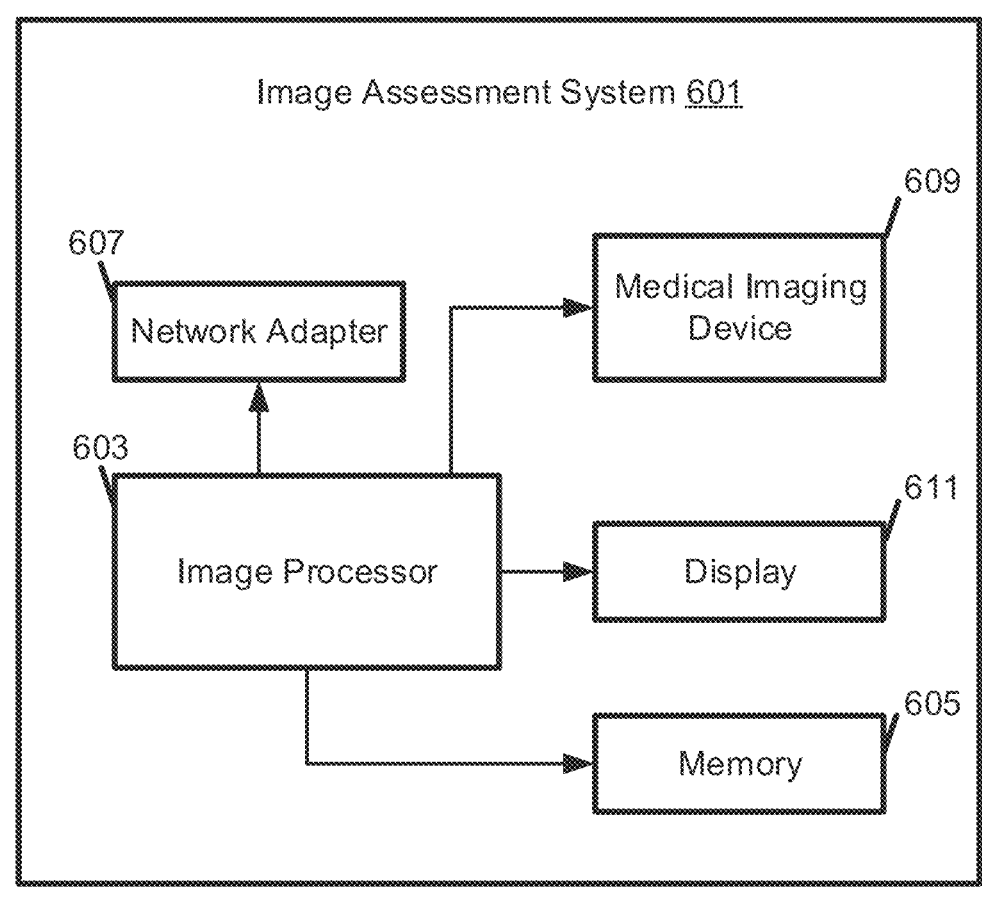
FIG. 6 is a block diagram of one embodiment of a medical image assessment system.

FIG. 6 is a block diagram of one embodiment of a medical image assessment system. The image assessment system 601 may include an image processor 603 coupled with a memory 605 and in communication with a network adapter 607, a medical imaging device 609, and a display 611.

The image assessment system 601, including one or more components 603-611 of the image assessment system 601, may be configured to perform one or more of the acts of FIG. 1, FIG. 2, FIG. 3, or other acts. The image assessment system 601 may be implemented in one or many different forms. For example, the image assessment system 601 may be implemented as a desktop computer program, a server based computer program, a mobile application, a cloud based service, or otherwise.

The image processor 603 may be a general purpose or application specific image processor. The image processor 603 may be configured to or may execute instructions that cause the image processor 603 to receive data, such as medical image data, auxiliary data, performance specifications, machine learning identities, and/or medical image results. The processor may receive the data via the network adapter 607, from the memory 605, from the medical imaging device 609, or from another device. The data may be generated by a medical imaging system or device. For example, the medical imaging device 609 or another medical imaging device or system may generate the medical image. The processor 603 may be further configured to apply the medical image and/or auxiliary data to a machine-learned classifier. The machine-learned classifier may be stored in the memory 605. In some cases, the machine-learned classifier may be received at the processor 603 via the network adapter 607. In some cases, the image processor 603 may be configured to train the machine learning classifier. For example, the image processor 603 may be configured to train the classifier according to FIG. 3. The image processor 603 may be further configured to generate performance specifications, machine learning identities, and/or medical image results based on applying the medical image and/or auxiliary data to the machine-learned classifier. The image processor 603 may be further configured to output the label performance specifications, machine learning identities, and/or medical image results.

The memory 605 may be a non-transitory computer readable storage medium. The memory 605 may be configured to store instructions that cause the image processor to perform an operation. For example, the memory 605 may store instructions that, when executed by the image processor 603, cause the image processor 603 to perform one or more acts of FIG. 1, FIG. 2, FIG. 3, or other acts. The memory 605 may be configured to store medical image data, auxiliary data, performance specifications, machine learning identities, medical image results, machine learning classifiers, machine-learned classifiers, or other information. The instructions for implementing the processes, methods, and/or techniques discussed herein are provided on non-transitory computer readable storage media or memories, such as a cache, buffer, RAM, removable media, hard drive, or other computer readable storage media. Non-transitory computer readable storage media include various types of volatile and nonvolatile storage media.

The network adapter 607 (e.g. a gateway) may be a software module executed by the image processor 603. In some cases, the adapter may be implemented by a separate image processor or by standalone hardware. The adapter 607 may be configured to receive and/or transmit medical image data, auxiliary data, performance specifications, machine learning identities, medical image results, machine learning classifiers, machine-learned classifiers, or other information between components of the image assessment system 601 and other components or systems. For example, the network adapter 607 may be in communication with a computer, a server, a medical imaging device, or other devices.

The medical imaging device 609 may be configured to generate medical image data. The medical imaging device may use an MR, CT, x-ray, or another imaging modality to generate images. The medical imaging device 609 may be configured to send the medical image data to one or more of the components of the image assessment system 601. For example, the medical imaging device 609 may send the images to the processor 603, the memory 605, the network adapter 607, or the display 611 directly or through one or more intermediaries.

The display 611 may be configured to accept user input and to display audiovisual information to the user. In some cases, the display 611 may include a screen configured to present the audiovisual information. For example, the display 611 may present the medical image data, selected performance specification, selected machine learning identity, and/or the medical image result. Via the display 611, users may review the medical image result to assess whether the result is correct for the medical image data. The display 611 may include a user input device. For example, the display may include a keyboard, mouse, and/or a virtual or augmented reality environment. In some cases, the user may input information relating to the auxiliary information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for assessing medical images, the method comprising:
  receiving, by a processor, first medical image data and first auxiliary patient data;
  identifying, by the processor, a plurality of machine-learned models tuned to various economic and clinical environments;
  inputting, by the processor, the first auxiliary patient data to a machine-learned classifier, the machine-learned classifier trained on second auxiliary patient data, wherein the second auxiliary patient data comprises at least indicators of clinical impact and economic impact for a particular region and/or a healthcare facility of the results generated by the plurality of machine-learned models;
  outputting, by the machine-learned classifier in response to inputting the first auxiliary patient data to the machine-learned classifier, a machine-learned model of the plurality of machine-learned models, wherein the machine-learned model or a performance specification for the machine-learned model is tuned to individual constraints of a particular environment described by the first auxiliary patient data;
  applying, by the processor, the first medical image data and the first auxiliary patient data to the machine-learned model;
  generating, by the processor, a medical image result of the first medical image data based on applying the first medical image data and the first auxiliary patient data to the machine-learned model; and
  outputting, by the processor, the medical image result.

2. The method of claim 1, wherein the medical image result comprises a label, a segmentation, a classification, a registration, a quantification, a fusion image, a simulation, or a combination thereof.

3. The method of claim 1, wherein the machine-learned model is a detection algorithm, a segmentation algorithm, a quantification algorithm, a model, a registration algorithm, a fusion algorithm, a simulation algorithm, or a combination thereof.

4. The method of claim 1, wherein performance specification comprises an operating characteristic curve, an operating point, or a combination thereof.

5. The method of claim 1, wherein the first auxiliary patient data comprises patient vital information, patient outcome statistics, available treatment options, medical treatment guidelines, length of stay, treatment cost, reimbursement codes, mistakes made, or a combination thereof.

6. The method of claim 1, wherein the first auxiliary patient data is received from a network interface in communication with a medical data repository.

7. The method of claim 1, further comprising:
  receiving, by the processor, further auxiliary patient data collected based on the medical image result; and
  updating, by the processor, the machine-learned model based on applying the further auxiliary patient data to the machine-learned classifier.

8. The method of claim 1, wherein the machine-learned classifier and the machine-learning model are integrated into a machine learning network, and
  wherein the first medical image data and first auxiliary patient data are applied to the machine learning network.

9. A medical image assessment system, the system comprising:
  an image processor, coupled with a memory containing instructions that, when executed, cause the image processor to:
  apply first auxiliary patient data to a machine-learned classifier;
  select, by the machine-learned classifier in response to applying the first auxiliary patient data, a machine-learned model from a plurality of machine-learned models, the selected machine-learned model tuned to individual constraints of a particular environment described by the first auxiliary patient data, wherein the machine-learned classifier is trained using at least second auxiliary patient data comprising at least indicators of clinical and economic impacts for a particular region and/or healthcare facility of the results generated by the plurality of machine-learned models;
  apply a first medical image to the selected machine-learned model; and
  generate an analysis of the first medical image based on the application of the first medical image to the machine-learned model.

10. The system of claim 9, wherein each machine-learned model of the plurality of machine-learned models is configured with a different operating characteristic curve of a plurality of operating characteristic curves.

11. The system of claim 9, wherein each machine-learned model of the plurality of machine-learned models is configured with a different operating point of a plurality of operating points.

12. A method for training a machine-learning model, the method comprising:
  receiving, by a processor, auxiliary patient data and a plurality of machine learning specifications associated with the auxiliary patient data that are tuned to specific environments related to the auxiliary patient data, wherein the auxiliary patient data comprises at least indicators of clinical and economic impact for a particular region and/or a healthcare facility;
  training with machine learning, by the processor, the machine-learning model based on the auxiliary patient data and the machine learning specifications, wherein a result of the training is a machine-learned model that is configured to output a machine learning specification from the plurality of machine learning specifications that is tuned to individual constraints of a particular environment; and storing, by the processor, the machine-learned model.

13. The method of claim 12, wherein the plurality of machine learning specifications comprises a plurality of operating characteristic curves.

14. The method of claim 12, wherein the plurality of machine learning specifications comprises a plurality of operating points.

15. The method of claim 12, wherein the plurality of machine learning specifications comprises a plurality of further machine-learned models.

16. The method of claim 12, further comprising:

applying, by the processor, second auxiliary patient data to the machine-learned model; and generating, by the processor, the output based on the applying, wherein the machine learning specification is based on the second auxiliary patient data.

17. The method of claim 12, further comprising:

receiving, by the processor, third auxiliary patient data collected based on the output; and updating, by the processor, the machine-learned model based on applying the third auxiliary patient data and the plurality of machine learning specifications to the machine-learned model.

* * * * *